United States Patent
Guo et al.

(10) Patent No.: US 8,895,933 B2
(45) Date of Patent: Nov. 25, 2014

(54) DATA ACQUIRED SYSTEM AND CT APPARATUS USING THE SAME

(75) Inventors: Jun Guo, Beijing (CN); Xiaoyan Zhang, Beijing (CN); Hailiang Liu, Beijing (CN); Zhuo Liu, Beijing (CN); Ashutosh Joshi, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 321 days.

(21) Appl. No.: 13/427,380

(22) Filed: Mar. 22, 2012

(65) Prior Publication Data

US 2012/0243661 A1 Sep. 27, 2012

(30) Foreign Application Priority Data

Mar. 23, 2011 (CN) .......................... 2011 1 0080253

(51) Int. Cl.
*A61B 6/03* (2006.01)
*A61B 6/00* (2006.01)

(52) U.S. Cl.
CPC ............... *A61B 6/035* (2013.01); *A61B 6/4266* (2013.01); *A61B 6/4488* (2013.01)
USPC ..................................... 250/363.02; 454/284

(58) Field of Classification Search
CPC ..... A61B 6/035; A61B 6/4266; A61B 6/4488
USPC ......... 250/363.02, 366, 370.08, 394; 454/284
See application file for complete search history.

(56) References Cited

U.S. PATENT DOCUMENTS

| | | | |
|---|---|---|---|
| 7,065,173 B2 | 6/2006 | Lacey et al. | |
| 7,236,562 B2 * | 6/2007 | Joshi et al. | ...................... 378/19 |
| 7,449,696 B2 | 11/2008 | Joshi et al. | |
| 7,512,209 B2 | 3/2009 | Joshi et al. | |
| 7,586,096 B2 * | 9/2009 | Astley et al. | ............. 250/370.15 |
| 7,806,590 B2 | 10/2010 | Jimbo et al. | |
| 2012/0152255 A1 * | 6/2012 | Barlow et al. | ............ 128/205.25 |

* cited by examiner

*Primary Examiner* — Mark R Gaworecki
(74) *Attorney, Agent, or Firm* — Armstrong Teasdale LLP

(57) ABSTRACT

A data acquired system is provided. The data acquired system includes a main structure with a cavity formed therein, the cavity having a bottom for mounting a circuit board with electrical components thereto, a fan assembly disposed on the main structure, and an airflow guide disposed within the cavity and configured to guide airflow from the fan assembly for heat dissipation of the electrical components, the airflow guide positioned at a distance above the electrical components to form a gap between the airflow guide and the electrical components, wherein a sidewall of the cavity is provided with an air vent corresponding to the gap such that the airflow passes through the gap and is discharged from the air vent.

20 Claims, 7 Drawing Sheets

DATA ACQUIRED SYSTEM AND CT APPARATUS USING THE SAME

CROSS REFERENCE TO RELATED APPLICATIONS

This application claims the benefit of Chinese Patent Application No. 201110080253.0 filed Mar. 23, 2011, which is hereby incorporated by reference in its entirety.

BACKGROUND OF THE INVENTION

The present invention relates to computerized tomography (CT), and in particular to a data acquired system (DAS) and a CT apparatus using the same.

A CT apparatus has been used for real time observation of the internal condition of an object. A typical CT apparatus includes an X-ray source configured to emit X-rays to a patient or luggage. A detector is installed on the other side of the object and configured to detect the X-rays passing through the object.

For instance, the CT apparatus measures a human body based on different absorption and penetration rates of different tissues for the X-rays, and then inputs the measured data into a computer which, after processing the data, can take a sectional or stereo image for the examined part of the body, thereby discovering tiny pathological changes of any part in the body.

A DAS is mainly used to receive the electrical signals acquired by the detector, and convert the signals into digital signals for subsequent processing. Certainly, the DAS is not limited to this use, and is sometimes employed in the subsequent processing. In some designs, the detector is directly integrated in the DAS.

U.S. Pat. No. 7,236,562 B2, which is hereby incorporated by reference in its entirety, discloses a method of assembly and thermal management of CT detector electronic circuits. FIGS. 1 and 2 of U.S. Pat. No. 7,236,562 B2 demonstrate the operating mode and principle of the CT apparatus and the DAS therein.

The DAS includes several circuit boards with electrical components. In the prior art, it is rather difficult to have uniform temperature distribution on different circuit boards and lower temperature on each circuit board.

BRIEF DESCRIPTION OF THE INVENTION

To solve the problem of heat dissipation of the data acquired system (DAS) in the prior art, the embodiments described herein provide a new DAS and a computerized tomography (CT) apparatus using the same. The DAS described herein has an efficient heat-dissipation capability, which on the one hand lowers the temperature of electrical components and extends the service life of the electrical components, on the other hand achieves higher temperature uniformity on circuit boards and has narrow temperature distribution on different electrical boards, thereby contributing to high CT image quality. Moreover, with less material and enough stiffness, the DAS described herein is adapted to be mounted on a rotating gantry of the CT apparatus.

In one aspect, a data acquired system (DAS) is provided. The DAS includes a main structure with a cavity formed therein, the cavity having a bottom for mounting a circuit board with electrical components, a fan assembly disposed on the main structure, and an airflow guide disposed within the cavity to guide airflow from the fan assembly for heat dissipation of the electrical components, the airflow guide being positioned at a distance above the electrical components to form a gap between the airflow guide and the electrical components, wherein a sidewall of the cavity is provided with an air vent corresponding to the gap such that the airflow passes through the gap and is discharged from the air vent.

As an exemplary embodiment, the airflow guide is shaped to taper a cross section of an airflow channel in a direction from the fan assembly to the electrical components.

As an exemplary embodiment, the airflow guide is disposed abutting the sidewall with the air vent and is formed into a wedge shape.

As an exemplary embodiment, a filter assembly is disposed between the main structure and the fan assembly for filtering incoming air.

As an exemplary embodiment, an electromagnetic interference (EMI) guard is disposed between the main structure and the fan assembly.

As an exemplary embodiment, a filter assembly integrated with an electromagnetic interference guard is disposed between the main structure and the fan assembly, and the integrated filter assembly is composed of an air filter foam plate and an anti-electromagnetic interference honeycomb plate clamped between front and rear plates.

As an exemplary embodiment, the main structure takes on an approximately arc shape and forms an approximately arc-shaped cavity therein.

As an exemplary embodiment, the approximately arc-shaped cavity of the main structure includes a radial inner wall, a radial outer wall forming the air vent thereon circumferentially, wherein two reinforcing support poles are disposed on the radial outer wall spaced apart from each other, thereby separating the air vent into three air outing windows, and two reinforcing walls disposed respectively at two ends of the cavity.

In another aspect, a CT apparatus including the aforesaid DAS is provided.

In another aspect, the present invention provides a CT apparatus comprising the aforesaid DAS.

It is to be particularly noted that the additional features in the DAS can be used either independently or in combination with one or more of any other additional features.

The embodiments described herein have at least the following advantages.

With regard to the rotating gantry, it is desired that the DAS mounted thereon uses less material and has enough stiffness. The embodiments described herein use a main support structure with two reinforced walls and two reinforced poles, thereby meeting the requirements for both material and stiffness. At the same time, using two poles does not occupy too much air vent area, and hence has no effect on the heat dissipation performance.

The guidance of the airflow guide and the tapering of the airflow channel direct the airflow from the fan completely to the electrical components and accelerate the airflow to be finally discharged from the air vent, thereby avoiding bypass and turbulence of the airflow and improving the heat dissipation efficiency. Consequently, different circuit boards have higher temperature uniformity and minor temperature difference, which contributes to high CT image quality.

The embodiments described herein effectively blow away heat dissipation from the electrical components, such that the electrical components in the DAS have lower working temperature, which will extend the service life of the electrical components.

With a filter assembly and an electromagnetic interference guard, the effective airflow of the DAS is compatible with electromagnetic (EMC), and has the dust-preventing performance.

As the main structure of the DAS takes on an approximately arc shape and forms an approximately arc-shaped cavity therein, the DAS of the embodiments described herein tends to be easily disposed on the annular gantry of the CT apparatus and has a large space for mounting the circuit boards.

The aforesaid and other characteristics of the embodiments described herein will be apparent with a survey of the detailed description of the following exemplary embodiments in combination with the accompanying figures and claims.

BRIEF DESCRIPTION OF THE DRAWINGS

Exemplary embodiments are specifically described hereunder with reference to the figures and in combination with the embodiments. The merits and implementing modes of the embodiments described herein will be more comprehensible with reference to the figures. It should be understood that the illustrations of the figures are only used to explain the embodiments described herein, and do not limit the embodiments described herein in any sense.

DETAILED DESCRIPTION OF THE INVENTION

Figure 1:
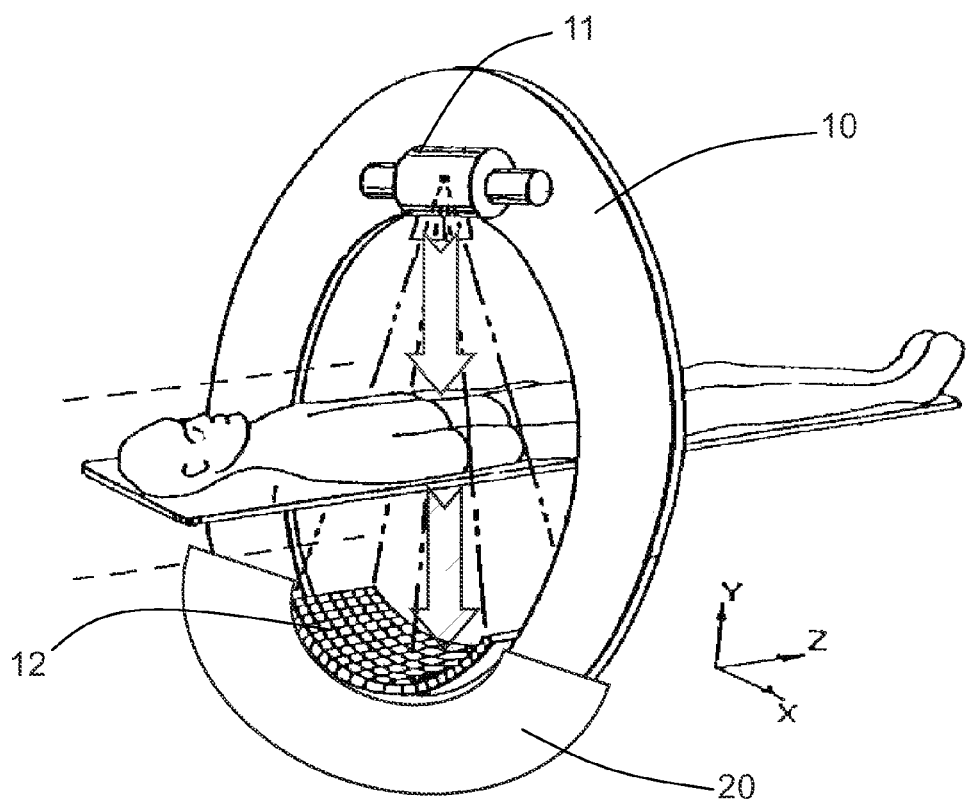
FIG. 1 schematically shows the operating principle of a CT apparatus and the position of a data acquired system (DAS) in the CT apparatus.

As shown in FIG. 1, the exemplary CT apparatus includes a rotatable annular gantry 10 having a hole through it, the hole being designed to receive a subject like a patient moving horizontally therethrough. The gantry 10 is provided with an X-ray source 11 configured to emit X-rays to the subject like a patient. A detector 12 is installed on the other side of the subject and configured to detect the X-rays passing through the subject. A data acquired system (DAS) 20 is disposed adjacent to the detector 12 on the same side as the gantry. The X-ray source 11 is installed on an annular section of the gantry 10 of the CT apparatus, opposing the detector 12 and the DAS 20. In the scanning process, the gantry rotates as necessary. Hence, it is desired that the DAS use less material and have enough stiffness.

Figure 2:
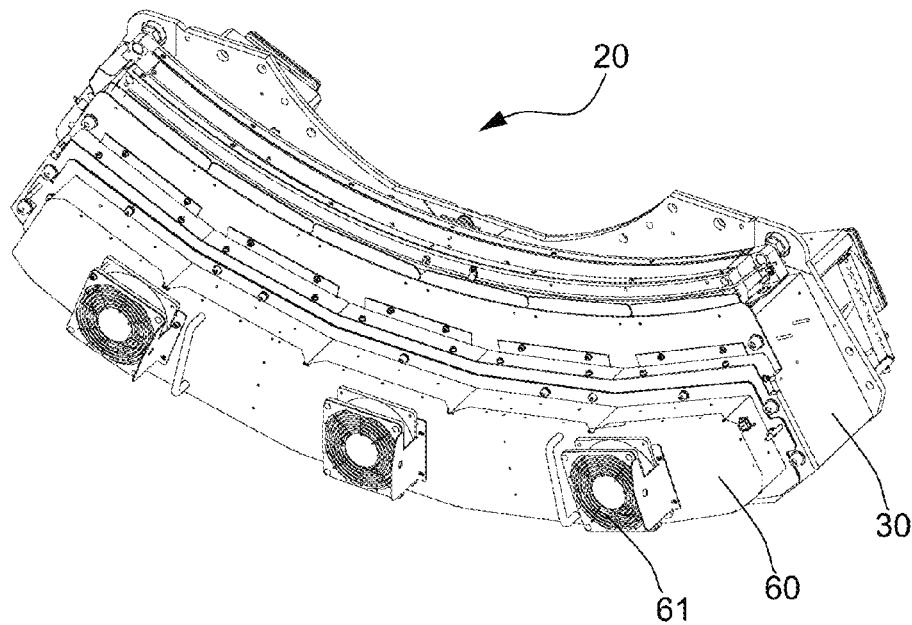
FIG. 2 is a schematic diagram of the overall structure of an exemplary DAS.
Figure 3:
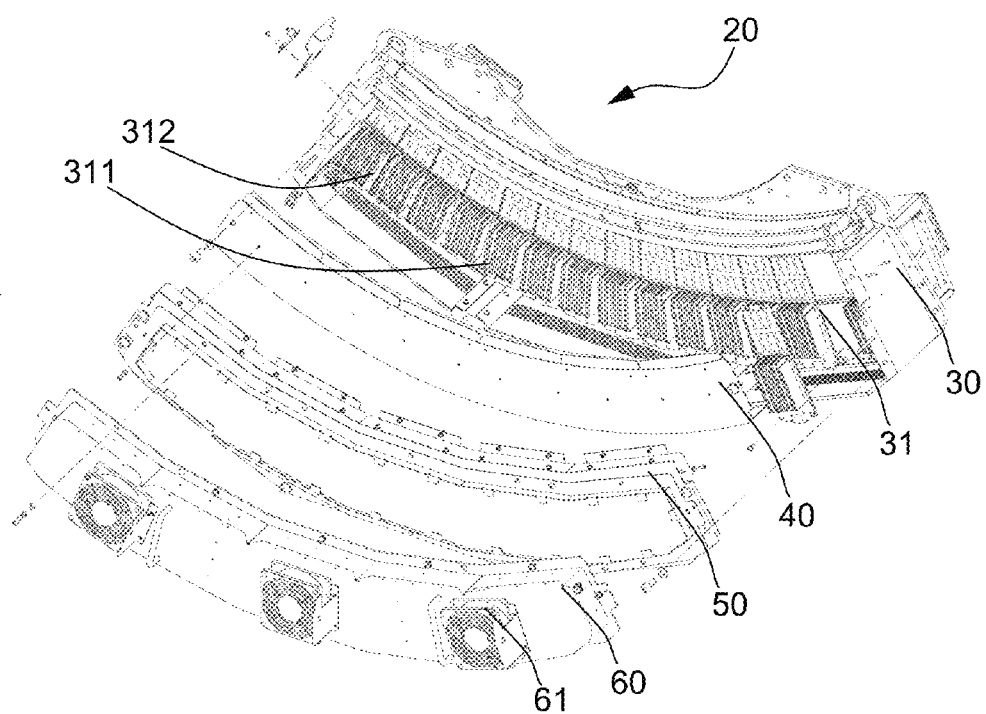
FIG. 3 is a schematic diagram of the exploded structure of the DAS shown in FIG. 2.
Figure 4:
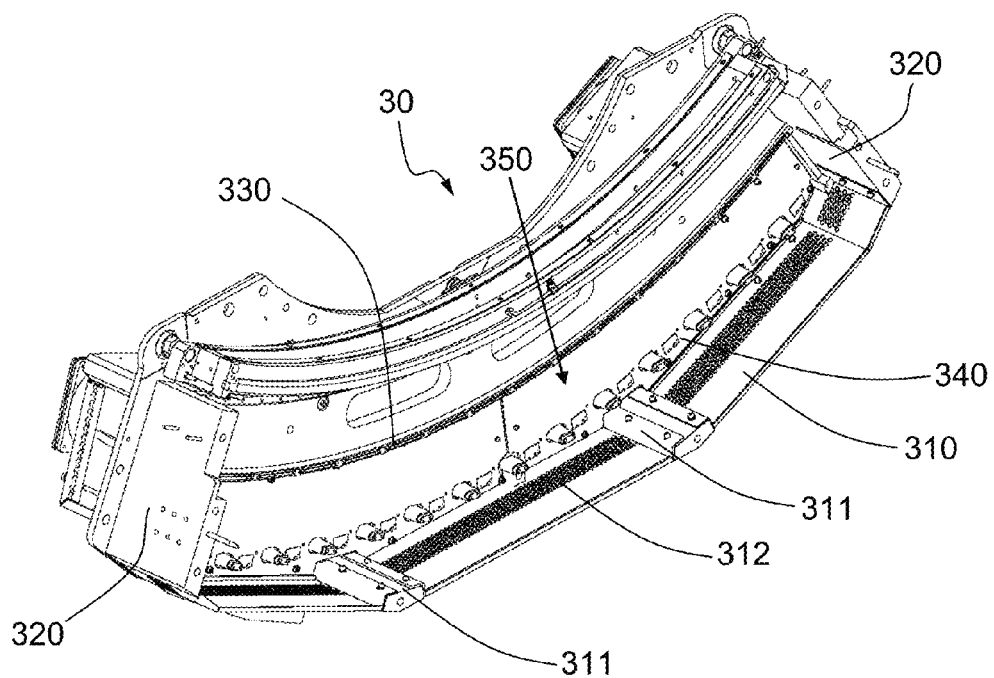
FIG. 4 is a diagrammatic view of the main structure of the DAS shown in FIG. 2 and FIG. 3.
Figure 5:
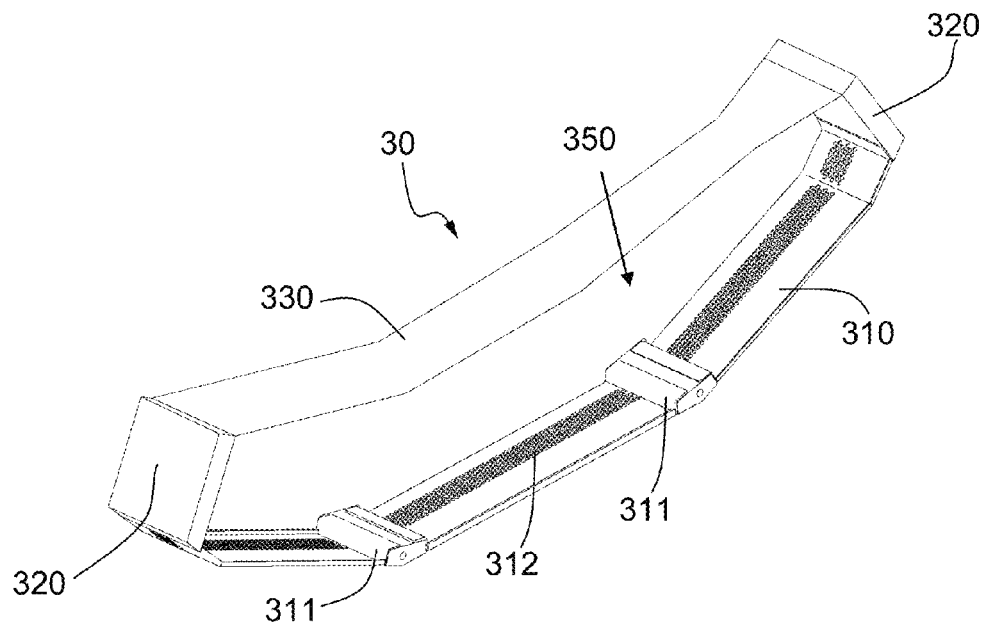
FIG. 5 shows the construction principle of the main structure of the DAS in FIG. 4.

FIGS. 2 and 3 show the overall structure of a DAS 20 in an exemplary embodiment. FIG. 4 shows the main structure of the DAS, and FIG. 5 shows the construction principle of the main structure of the DAS. The DAS 20 includes a main structure 30 with a cavity 350 formed therein, a bottom 340 of the cavity 350 being used for mounting circuit boards with electrical components 31. The DAS 20 further includes a fan assembly 60 disposed on the main structure 30, and an airflow guide 40 disposed within the cavity 350 to guide airflow from the fan assembly 60 for heat dissipation of the electrical components 31. The airflow guide 40 is positioned at a distance above the electrical components 31 to form a gap between the airflow guide 40 and the electrical components 31. A sidewall (namely a radial outer wall 310 in the exemplary embodiment) of the cavity 350 is provided with an air vent 312 corresponding to the gap (see FIGS. 11 and 12) such that the airflow passes through the gap and is discharged from the air vent 312. The heat-dissipation principle of the DAS 20 will be further described hereunder in combination with FIGS. 11 and 12. For example, FIG. 3 also shows an integrated filter assembly 50 with an electromagnetic interference (EMI) guard which shall be specifically described below. The fan assembly 60 includes at least one fan 61 installed on an approximately arc-shaped support structure. Three fans are used in the exemplary embodiment.

FIGS. 4 and 5 show that, in the exemplary embodiment, the main structure 30 takes on an approximately arcuate shape and forms an approximately arc-shaped cavity 350 therein. The approximately arc-shaped cavity 350 of the main structure comprises a radial inner wall 330 (which may also be formed after other components are mounted, and a radial outer wall 310 forming the air vent 312 thereon circumferentially. Two reinforcing support poles 311 are disposed on the radial outer wall 310 spaced apart from each other, thereby separating the air vent 312 into three air outing windows. The cavity 350 further includes two reinforcing walls 320 disposed respectively at the two ends of the cavity. With two walls 320, the support of two poles 311, one air inlet and three air outing windows, the DAS 20 uses less material and has enough stiffness. At the same time, using two poles 311 does not occupy too much air vent area, and hence has no effect on the heat dissipation performance.

Figure 6:
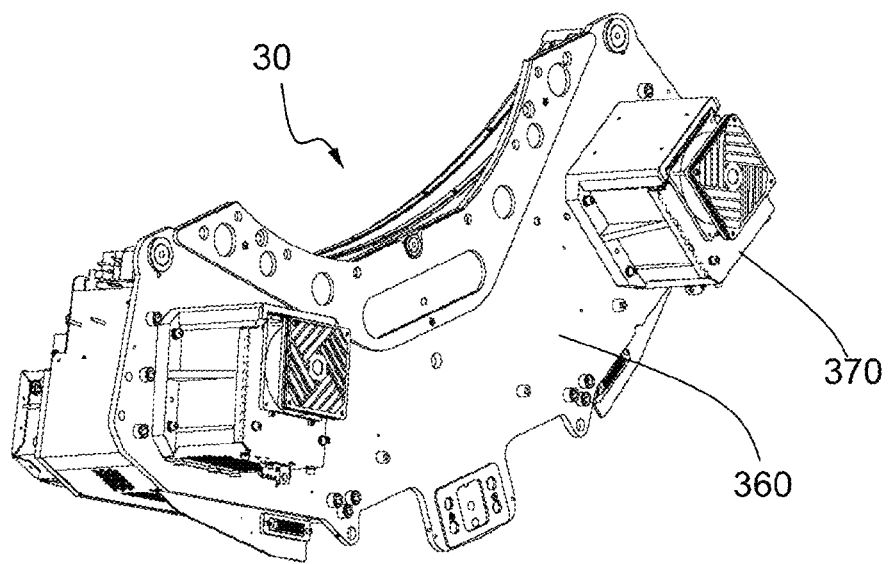
FIG. 6 is a diagrammatic view of the rear of the main structure of the exemplary DAS.

As shown in FIG. 3, a number of circuit boards with electrical components 31 can be mounted at the bottom 340 of the cavity 350. The electrical components 31 may have heat-dissipation fins to improve the heat-dissipation efficiency. FIG. 6 is a diagrammatic view of the rear of the main structure 30 of the exemplary DAS 20. On a rear 360 of the bottom 340 of the cavity 350, other electrical components 370 can also be disposed to dissipate heat and be cooled in an individual manner.

Figure 7:
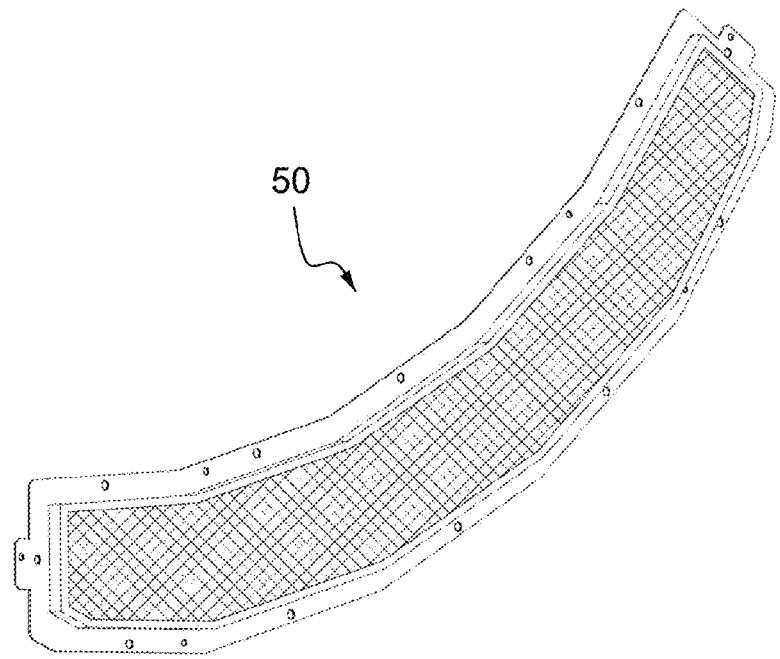
FIG. 7 is an overall schematic diagram of an exemplary integrated filter assembly.
Figure 8:
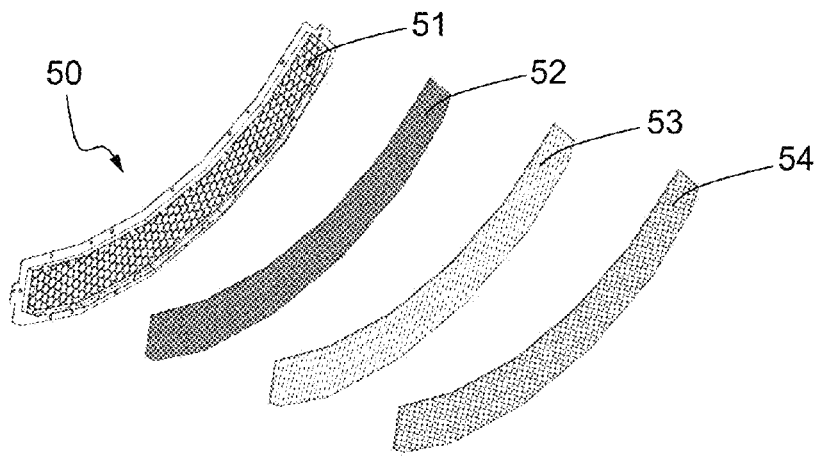
FIG. 8 is a schematic diagram of the exploded structure of the exemplary integrated filter assembly.

As shown in FIGS. 7 and 8, in the exemplary embodiment, a filter assembly 50 is disposed between the main structure 30 and the fan assembly 60 for filtering incoming air. In some embodiments, an electromagnetic interference guard is also disposed between the main structure 30 and the fan assembly 60. In the embodiment shown in FIGS. 7 and 8, the electromagnetic interference guard is integrated in the filter assembly 50. The integrated filter assembly 50 is composed of an air filter foam plate 53 and an anti-electromagnetic interference honeycomb plate 52 clamped between front and rear plates 51 and 54, wherein the plate 51 forms a support frame to be mounted on the main structure 30. The filter structure with EMC not only achieves electromagnetic compatibility, but also performs the functions of preventing dust and averaging airflow.

Figure 9:
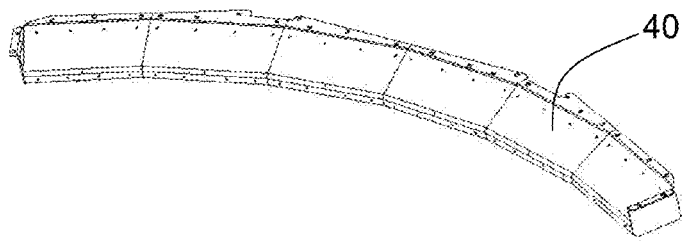
FIG. 9 is a perspective diagram of an exemplary airflow guide.
Figure 10:
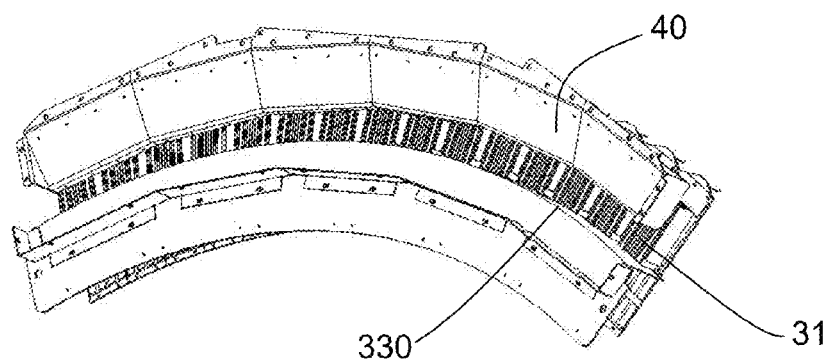
FIG. 10 is a schematic diagram of an airflow channel after installing the electrical components and the airflow guide in the main structure of the DAS, showing a tapering airflow channel.

FIG. 9 is a perspective diagram of an exemplary airflow guide, and FIG. 10 is a schematic diagram of an airflow channel after installing the electrical components and the airflow guide in the main structure 30 of the DAS 20, showing a tapering airflow channel. The airflow guide 40 is disposed abutting the sidewall 310 with the air vent 312 (see FIGS. 11 and 12) and is shaped to taper the cross section of the airflow channel in a direction from the fan assembly 60 to the electrical components. In the exemplary embodiment, the airflow guide 40 is formed into a wedge shape. As shown in FIG. 10, the guidance of the airflow guide 40 and the convergence or tapering of the airflow channel direct the airflow from the fan 61 completely to the electrical components 31 and accelerate the airflow to be finally discharged from the air vent 312, thereby avoiding bypass and turbulence of the airflow and improving the heat dissipation efficiency. Consequently, different circuit boards have higher temperature uniformity and relatively low temperature difference, which contributes to high CT image quality.

Figure 11:
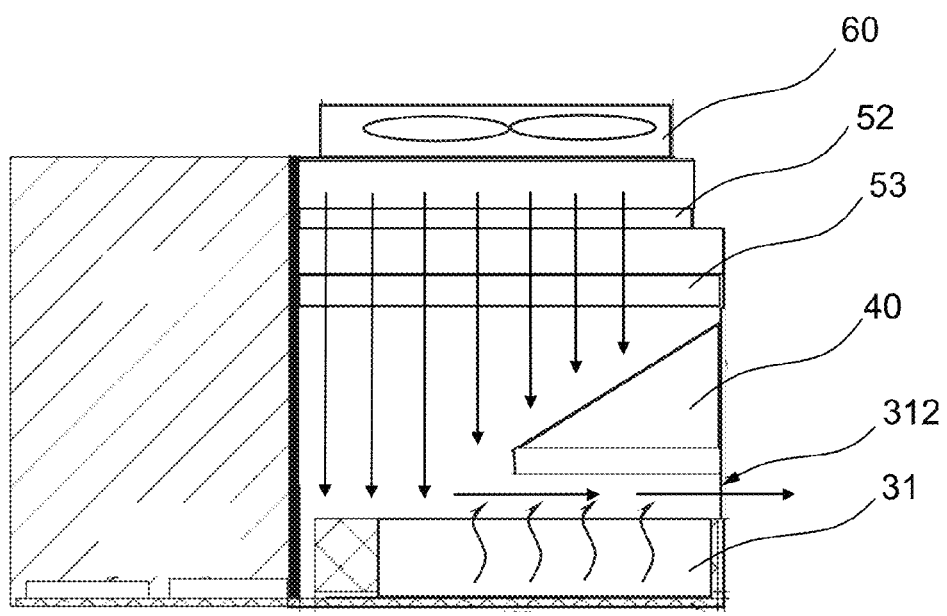
FIG. 11 is a schematic diagram of an exemplary heat-dissipation solution.

FIG. 11 shows the principle of an exemplary heat-dissipation solution, wherein air from the fan assembly 60 passes through the filter assembly (such as an anti-electromagnetic interference honeycomb plate 52 and an air filter foam plate 53) with EMC towards the electrical components 31. The airflow direction is indicated by the linear arrows shown in FIG. 11. In the airflow channel, the airflow guide 40 directs all the airflow to the electrical components 31 to take away the heat on the surface of the electrical components 31. The heat is discharged as the curvilinear arrows indicate in FIG. 11. The airflow then flows through the gap between the airflow guide 40 and the electrical components 31 to be finally discharged from the air vent 312.

Figure 12:
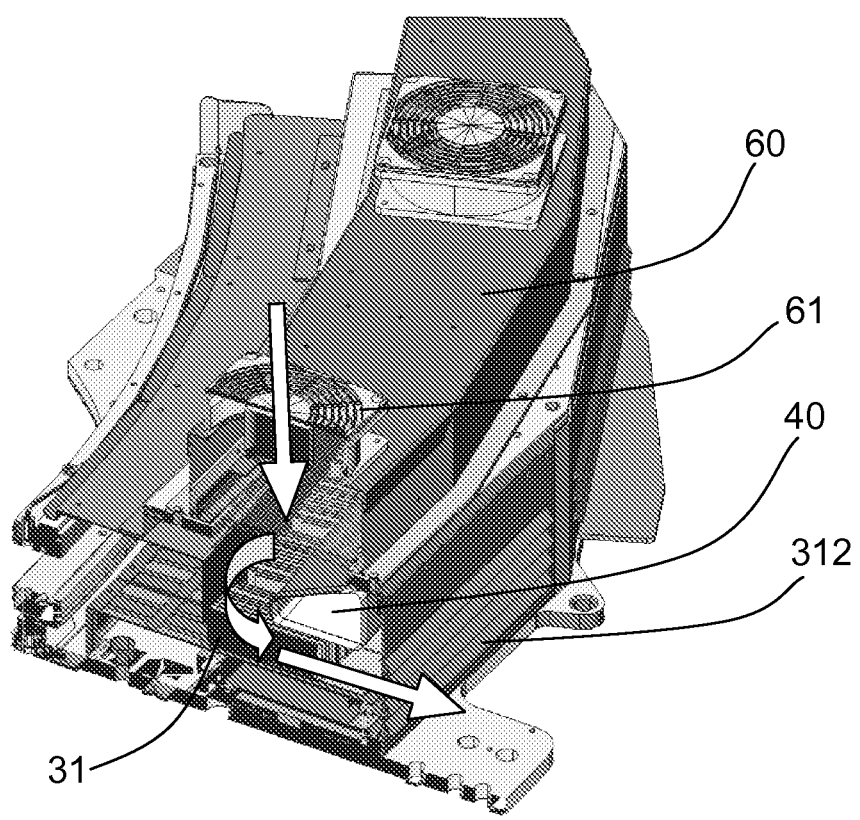
FIG. 12 is a sectional view of the airflow channel in the exemplary DAS, showing the flow path of the airflow.

FIG. 12 clearly shows the position of the airflow guide 40 in the airflow channel and the flow path of the airflow, as indicated by the arrows in FIG. 12. The air vent 312 can be in the form of mesh, louver or another configuration.

In some embodiments, a CT apparatus includes the DAS 20 described herein. The additional features in the DAS can be used either independently or in combination with one or more of any other additional features.

It is to be understood, however, that even though exemplary embodiments of the present invention have been set forth in the foregoing description with reference to the accompanying drawings, the embodiments specifically described herein are exemplary only, and do not limit the claim scope of the present invention. Skilled persons in the art can employ many modified solutions to carry out the present invention without departing from the essence and spirit of the present invention. These equivalent modifications based on the description and drawings all fall within the scope of the present invention defined by the claims.

What we claim is:

1. A data acquired system, comprising:
a main structure with a cavity formed therein, the cavity having a bottom for mounting a circuit board with electrical components thereto;
a fan assembly disposed on the main structure; and
an airflow guide disposed within the cavity and configured to guide airflow from the fan assembly for heat dissipation of the electrical components, the airflow guide positioned at a distance above the electrical components to form a gap between the airflow guide and the electrical components, wherein a sidewall of the cavity is provided with an air vent corresponding to the gap such that the airflow passes through the gap and is discharged from the air vent.

2. The data acquired system according to claim 1, wherein the airflow guide is shaped to taper a cross section of an airflow channel in a direction from the fan assembly to the electrical components.

3. The data acquired system according to claim 2, wherein the airflow guide is disposed abutting the sidewall with the air vent and is formed into a wedge shape.

4. The data acquired system according to claim 1, wherein a filter assembly is disposed between the main structure and the fan assembly for filtering incoming air.

5. The data acquired system according to claim 1, wherein an electromagnetic interference guard is disposed between the main structure and the fan assembly.

6. The data acquired system according to claim 1, wherein a filter assembly integrated with an electromagnetic interference guard is disposed between the main structure and the fan assembly, and the integrated filter assembly is composed of an air filter foam plate and an anti-electromagnetic interference honeycomb plate clamped between front and rear plates.

7. The data acquired system according to claim 1, wherein the main structure takes on an approximately arcuate shape and forms an approximately arc-shaped cavity therein.

8. The data acquired system according to claim 7, wherein the approximately arc-shaped cavity of the main structure comprises:
a radially inner wall;
a radially outer wall forming the air vent thereon circumferentially, wherein two reinforcing support poles are disposed on the radial outer wall spaced apart from each other, thereby separating the air vent into three air outing windows; and
two reinforcing walls disposed at two respective ends of the cavity.

9. The data acquired system according to claim 8, wherein the fan assembly comprises at least one fan installed on an approximately arc-shaped support structure.

10. A computerized tomography apparatus comprising a data acquired system, the data acquired system comprising:
a main structure with a cavity formed therein, the cavity having a bottom for mounting a circuit board with electrical components thereto;
a fan assembly disposed on the main structure; and
an airflow guide disposed within the cavity and configured to guide airflow from the fan assembly for heat dissipation of the electrical components, the airflow guide positioned at a distance above the electrical components to form a gap between the airflow guide and the electrical components, wherein a sidewall of the cavity is provided with an air vent corresponding to the gap such that the airflow passes through the gap and is discharged from the air vent.

11. The computerized tomography apparatus according to claim 10, wherein the airflow guide is shaped to direct the airflow from the fan assembly to the electrical components.

12. The computerized tomography apparatus according to claim 11, wherein the airflow guide is disposed abutting the sidewall with the air vent and is formed into a wedge shape.

13. The computerized tomography apparatus according to claim 10, wherein a filter assembly is disposed between the main structure and the fan assembly for filtering incoming air.

14. The computerized tomography apparatus according to claim 10, wherein an electromagnetic interference guard is disposed between the main structure and the fan assembly.

15. The computerized tomography apparatus according to claim 10, wherein a filter assembly integrated with an electromagnetic interference guard is disposed between the main structure and the fan assembly, and the integrated filter assembly is composed of an air filter foam plate and an anti-electromagnetic interference honeycomb plate clamped between front and rear plates.

16. The computerized tomography apparatus according to claim 10, wherein the main structure takes on an approximately arcuate shape and forms an approximately arc-shaped cavity therein.

17. The computerized tomography apparatus according to claim 16, wherein the approximately arc-shaped cavity of the main structure comprises:
   a radially inner wall;
   a radially outer wall forming the air vent thereon circumferentially, wherein two reinforcing support poles are disposed on the radial outer wall spaced apart from each other, thereby separating the air vent into three air outing windows; and
   two reinforcing walls disposed at two respective ends of the cavity.

18. The computerized tomography apparatus according to claim 17, wherein the fan assembly comprises at least one fan installed on an approximately arc-shaped support structure.

19. A method of assembling a data acquired system, the method comprising:
   mounting a circuit board to a bottom of a cavity of a main structure, the circuit board including electrical components;
   coupling a fan assembly to the main structure; and
   coupling an airflow guide within the cavity, the airflow guide configured to guide airflow from the fan assembly to dissipate heat generated by the electrical components, the airflow guide positioned at a distance above the electrical components to form a gap between the airflow guide and the electrical components, wherein a sidewall of the cavity is provided with an air vent corresponding to the gap such that the airflow passes through the gap and is discharged from the air vent.

20. The method of assembling a data acquired system according to claim 19, the method further comprising coupling a filter between the main structure and the fan assembly.

* * * * *